United States Patent [19]

Kaplan et al.

[11] 4,076,744

[45] Feb. 28, 1978

[54] AMPHOTERIC SURFACTANTS

[75] Inventors: Saul Kaplan, Teaneck; John J. Merianos, Jersey City, both of N.J.; Harold A. Green, Havertown, Pa.; Alfonso N. Petrocci, Glen Rock, N.J.

[73] Assignee: Kewanne Industries, Inc., Bryn Mawr, Pa.

[21] Appl. No.: 799,697

[22] Filed: May 23, 1977

[51] Int. Cl.[2] ........................ C07C 143/15; C11D 3/48

[52] U.S. Cl. ........................... 260/501.19; 260/501.21; 260/513 R; 260/513 B; 260/534 R; 252/89 R; 252/106; 252/525; 252/527; 252/529; 252/544; 252/546; 252/548

[58] Field of Search .......... 260/513 N, 501.19, 501.21

[56] References Cited

U.S. PATENT DOCUMENTS

| | | | |
|---|---|---|---|
| 2,452,043 | 10/1948 | Flett | 260/513 N |
| 3,833,590 | 9/1974 | Dazzi | 260/513 N |
| 4,001,285 | 1/1977 | Hochreuter | 260/513 N |

*Primary Examiner*—Nicky Chan

*Attorney, Agent, or Firm*—Arthur A. Jacobs

[57] ABSTRACT

Non-irritant amphoteric surfactants having the formula:

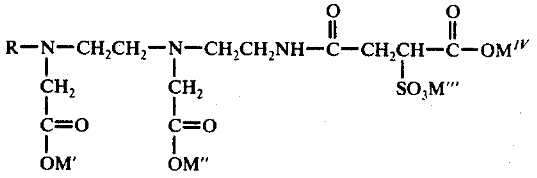

having preservative properties and compatible with anionic surfactants, where R is an alkyl group of from 8 to 14 carbon atoms, and where M' M'', M''' and $M^{IV}$ may be the same or different and represent a monovalent moiety selected from the group consisting of hydrogen, alkali metal, ammonium ion, or ammonium ion which is substituted by from 1 to 3 lower alkyl groups, said alkyl groups being optionally substituted by one hydroxyl group.

1 Claim, No Drawings

AMPHOTERIC SURFACTANTS

Amphoteric surfactants are advantageous components for inclusion in foaming and lathering compositions that are meant for personal use because, generally, they are less irritating to the skin than anionic or nonionic surfactants. A few ampholytes display such a low degree of eye irritancy that they are used in hair shampoos.

However, most ampholytes suffer from many shortcomings. Though they may have anti-microbial properties in freshly made aqueous solutions, they often lose these properties on standing, either gradually or precipitously; and though they may prevent the proliferation of microorganisms, they usually fail to kill all the microorganisms that are present. Such amphoteric surfactants, furthermore, have poor preservative properties and therefore must be used in combination with a preservative.

In addition, most ampholytes do not foam or lather well enough to be used as the sole foaming or lathering agent in cleansing preparation, such as shampoos, where much foam is required. Consequently, they must be used in combination with very much better foaming agents, such as anionic surfactants or non-ionic surfactants. In this respect, although, in principle, the shortcomings may be alleviated by the additives, in practice, the use of additives cause other problems; for example, good preservatives are not only costly, but often act as eye irritants. Furthermore, anionic surfactants are seldom compatible with concentrated amphoteric unless the anionic surfactant is present in concentrations considerably less than that of the ampholyte. An amphoteric surfactant that is present in aqueous solution at about 7½% or greater can seldom accomodate more than about one half of its weight of anionic surfactant without separating into two layers.

Furthermore, it is well known that the addition of comparatively large quantities of anionic surfactants often destroy the antimicrobial or preservative properties of other surfactants, especially when the concentration of anionic approximates the concentrations of the preservative surfactant.

It is therefore an object of this invention to provide an amphoteric surfactant which has good foaming properties.

It is another object of this invention to provide an amphoteric surfactant which is non-irritating to the skin and eyes.

It is another object of this invention to provide an amphoteric surfactant which can act as its own preservative in concentrations of 7½% or greater by weight.

It is another object of this invention to provide an amphoteric surfactant which is compatible with anionic surfactants so that concentrations of said ampholyte of 7½% or more by weight in aqueous solution can accommodate as much as an equal quantity of anionic surfactant in a single homogeneous phase.

It is a further object of this invention to provide an amphoteric surfactant which in concentrations of 7½% by weight is compatible with as much as an equal concentration of anionic without losing its anti-microbial activity, and without losing its preservative property.

Other objectives of the present invention will become apparent to one skilled in the art in the following description.

In accordance with the present invention, it has been discovered that compounds having the structural formula:

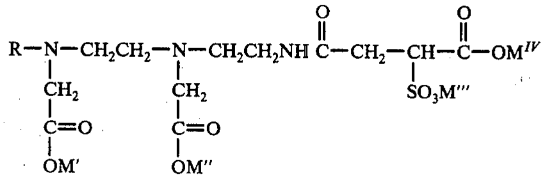

where R is an alkyl group of from 8 to 14 carbon atoms, and where M', M'', M''', $M^{IV}$ may be the same or different and constitute monovalent moieties selected from the group consisting of hydrogen, alkali metal, ammonium ion and ammonium ion that is substituted by from 1 to 3 lower alkyl groups, each of from one to three carbon atoms, and wherein each of said alkyl groups is optionally substituted by one hydroxyl group, are amphoteric surfactants with good foaming properties.

It has also been discovered that these ampholytes are nonirritants to the skin, and to the eyes.

It has further been discovered that these amphoteric surfactants have good anti-microbial properties and can act as preservatives in concentrations of 7½% by weight, or higher.

It has, in addition, been discovered that 7½% by weight concentrations of these ampholytes can accomodate up to an equal quantity of anionic surfactant without separating into two phases.

It has also been discovered that concentrations of 7½% by weight of these ampholytes retain their anti-microbial and preservative properties even in the presence of anionic surfactants whose concentration is as high as, or lower than, the concentration of ampholyte.

It has also been discovered that when the products disclosed in the following Examples 3 and 4 are substituted by only one carboxymethyl group instead of two carboxymethyl groups as shown in Examples 5 and 6, the products having only one carboxymethyl substituent have the same lathering, non-irritant, compatibility, and preservative properties as the products disclosed in Examples 5 and 6 which have two carboxymethyl substituents.

EXAMPLE 1

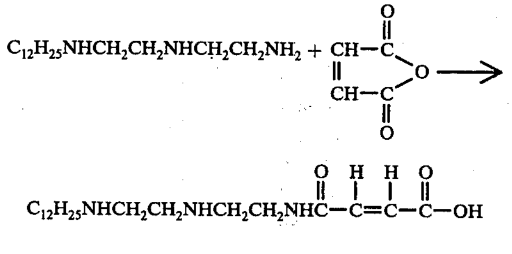

155 grams of N-dodecyl diethylenetriamine (0.57 moles) are dissolved in 57 grams of isopropanol with the aid of a little heat, and 57 grams of maleic anhydride (0.58 moles) are dissolved in 57 grams of isopropanol with the aid of a little heat.

With both solutions at a temperature slightly below 50° C, the maleic anhydride solution is added to the amine solution in small increments, over a period of about ½ hour, with constant stirring. An ice bath is used to keep the temperature of the reaction mixture below about 50° C, but the reaction temperature is kept above about 40° C to speed up the reaction.

After addition is complete, the reaction mixture is kept at about 35°–40° C with constant stirring for about 1½ hours.

The mixture weighs 328 grams. Upon analysis, it was found to contain about 1.79 milli-equivalents of free carboxylic acid groups per gram. The calculated concentrations for free carboxylic acid groups is 1.74 milli-equivalents per gram. The slight excess of carboxylic acid groups over theory was due to the 0.01 mole excess of maleic anhydride reactant which accounts for 2 milli-equivalents of free carboxylic acid group per millimole of anhydride.

The analysis can be interpreted to means that the yield is about 100%.

EXAMPLE 2

The reaction of Example 1 is repeated, except that N-decyl diethylenetriamine and N-tetradecyl diethylenetriamine respectively replace N-dodecyl diethylenetriamine as a reactant, all reactants being used in about the same molar ratios. The results duplicate those found in Example 1.

EXAMPLE 3

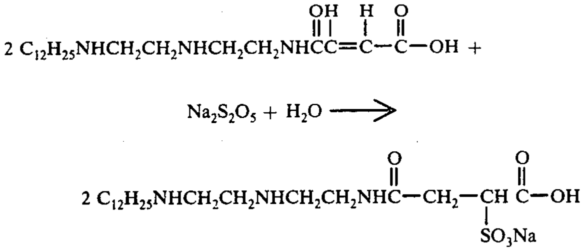

200 grams of the final mixture product of Example 1, without further purification, are dissolved in about 100 grams of water and warmed to about 40° C, at which temperature 33 grams of solid $Na_2S_2O_5$ is added in one increment. This raises the temperature only slightly so the mixture is heated, with stirring, to 66° C, and kept at about that temperature for 2 hours. The final mixture weighs 328 grams.

Calculations indicated that it contains about 2.15 milliequivalents of free available amine per gram.

EXAMPLE 4

The reaction of Example 3 is repeated, except that each of the two products in Example 2 replaces the product of Example 1, all reactants being used in about the same molar ratios. The results are similar to those of Example 3.

EXAMPLE 5

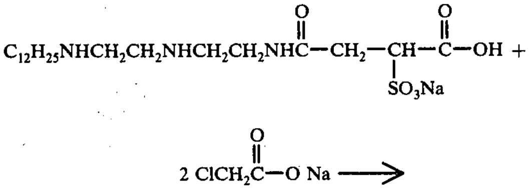

-continued

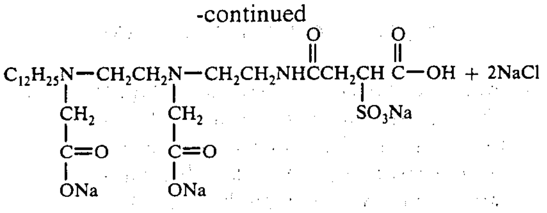

To 192 grams of the product mixture from Example 2 (containing about 415 milli-equivalents of free available amino nitrogen) is added 53.8 grams of 97% pure sodium chloroacetate (about 428 millimoles) which represent about 1 milli-equivalent of sodium chloroacetate for every milli-equivalent of free available amino nitrogen, plus about 3% of excess.

The mixture is warmed gently and the pH taken about every 10 minutes using a calomel electrode. As the reaction proceeds the pH drops but it is restored continuously by the dropwise addition of about 30% aqueous sodium hydroxide solution. In this manner, the reaction is run at a temperature of about 85° C while the pH is maintained between 6.7 and 8.0.

Ionic chloride determinations are made periodically to estimate the extent of the reaction, and the reaction is considered complete when the analysis for ionic chloride is equal to the calculated amount, which in this case, is about 415 milli-equivalents in the entire mixture.

The reaction is completed in about 5 hours. As it nears completion, the pH of the reaction mixture remains almost constant.

EXAMPLE 6

The reaction of Example 5 is repeated except that each of the two products in Example 4 replaces the product from Example 3, all reactants being used in about the same molar ratios. The results are similar to those of Example 5.

EXAMPLE 7

Eye irritation was determined by the procedure suggested by Dr. Draize as described in "Appraisal of the Safety of Chemicals in Foods, Drugs, and Cosmetics" published by the Association of Food and Drug Officials of the United States.

Each of three normal healthy albino rabbits had 0.1 ml. of 7½% solids, in aqueous solution, of the compound of Example 5, instilled into the right eye, with no further subsequent treatment. The left eye of each animal was left untreated and was used as a control.

Both eyes were examined every 24-hours for 4 days, and again on the seventh day; these observations were recorded on the Draize scale for scoring occular lesions. All recordings were zero for all observations on each animal with regard to changes in cornea, changes in iris, and conjunctivitis.

The test was repeated with another batch of material made as described in Examples 1, 3 and 5. The results were identical.

The compositions were tested for preservative ability in the following manner:

50 gram samples from each composition were transferred to sterile 4-ounce, wide-mouth jars. Two replicate jars were prepared for every sample, including an untreated control.

Each jar was inoculated with 2.5 ml. of a 1/10 sterile nutrient heated dilution of pooled 24-hour broth cultures of Staphylococcus aureus, Pseudomonas aeruginosa, Escherichia coli, Enterobacter aerogenes, Proteus species and Bacillus species. In this manner, a bacterial challenge load of (1–10) × $10^6$ organisms/ml. of jar content was obtained.

All inoculated jars were stored at 25° C–27° C. At weekly intervals following inoculation, a one ml. aliquot of jar content was removed from each jar, and a tenfold serial dilution was prepared therefrom in sterile "Azlectin"/"Tween 80" neutralizer solution which was then placed into a TGE jar.

In this manner, the number of surviving organisms was determined.

All jars were stored for 8 consecutive weeks, and weekly platings were prepared therefrom for the purpose of counting the surviving viable bacteria. Adequate preservation was considered to be achieved when 99.9% of the organism load used to inoculate the sample were killed.

In those instances where no viable surviving organisms were observed at four weeks following inoculation or before, the jar contents were re-inoculated after the fourth week exactly as previously described in the inoculation procedure.

Four additional weekly platings and countings were made for each jar, making a total of 8 consecutive weekly observations following the initial inoculation.

Following is a table showing the results of the tests for preservation. The bacterical count after each week is listed for each of the products tested. The asterisk indicates that the number must be multiplied by $10^6$.

In this table, the following designations represent the products under test and the conditions under which they were tested:

C-10 represents the compound of the present invention in which R is the decyl chain.
C-12 represents the compound of the present invention in which R is the dodecyl chain.
C-10/12 represents a 50/50 mixture C-10 and C-12.
A represents 7½% aqueous solution of C-10.
B represents 7½% aqueous solution of 5 parts of C-10 to 1 part of sodium lauryl sulfate.
C represents 7½% aqueous solution of equal parts of C-10 and sodium lauryl sulfate.
D represents a 7½% aqueous solution of C-12.
E represents a 7½% aqueous solution of 3 parts of C-12 to 1 part of sodium lauryl sulfate.
F represents a 7½% aqueous solution of 5 parts of C-12 to 1 part of sodium lauryl sulfate.
G represents a 7½% aqueous solution of C-12 stored at 30° C.
H represents a 12½% aqueous solution of C-12 stored at 30° C.
I represents a 12½% aqueous solution of equal parts of C-12 and sodium lauryl sulfate, stored at 30° C.
J represents a 12½% aqueous solution of 3 parts of C-12 to 1 part of sodium lauryl sulfate stored at 30° C.
K represents a 12½% aqueous solution of 5 parts of C-12 to 1 part of sodium lauryl sulfate stored at 30° C.
M represents a 7½% solution of C-12 stored at 24° C.
N represents a 7½% solution of three parts of C-12 to 1 part of sodium lauryl sulfate stored at 24° C.
O represents a 7½% aqueous solution of C-10 stored at 24° C.

P represents a 7½% aqueous solution of three parts of C-10 to 1 part of sodium lauryl sulfate, stored at 24° C.
Q represents a 7½% aqueous solution of C-12 stored at 24° C.
R represents a 12½% aqueous solution of C-12 stored at 24° C.
S represents a 12½% aqueous solution of equal parts of C-12 and sodium lauryl sulfate stored at 24° C.
T represents a 12½% aqueous solution of 3 parts of C-12 to one part of sodium lauryl sulfate stored at 24° C.
U represents a 12½% aqueous solution of 5 parts of C-12 to one part of sodium lauryl sulfate stored at 24° C.
V represents a 12½% aqueous solution of 3 parts of C-12 to one part of ammonium lauryl sulfate stored at 24° C.
W represents a 7½% aqueous solution of C-12 stored at 28° C.
X represents a 7½% aqueous solution of 3 parts of C-12 to one part of sodium lauryl sulfate stored at 28° C.
Y represents a 7½% aqueous solution of C-10 storead at 28° C.
Z represents a 7½% aqueous solution of 3 parts of C-10 to 1 part of sodium lauryl sulfate stored at 28° C.
AA represents a 7½% aqueous solution of equal parts of C-10/12.
BB represents a 7½aqueous solution of 3 parts of C-10/12 to 1 part of sodium lauryl sulfate.
CC represents a 7½% aqueous solution of C-10/12.
DD represents a 9% aqueous solution of C-10/12.
EE represents a 10½% aqueous solution of of C-10/12.
FF represents a 12½% aqueous solution of C-10/12.
GG represents a 13½% aqueous solution of C-10/12.
HH represents a 15% aqueous solution of C-10/12.
II represents a 15% aqueous solution of 1 part of C-10/12 to 1 part of sodium lauryl sulfate.
JJ represents a 15% aqueous solution of 3 parts of C-10/12 to 1 part of sodium lauryl sulfate.
KK represents a 15% aqueous solution of 5 parts of C-10/12 to 1 part of sodium lauryl sulfate.
LL represents a 7½% aqueous solution of C-12.
MM represents a 9% aqueous solution of C-12.
NN represents a 10½% aqueous solution of C-12.
OO represents a 12% aqueous solution of C-12.
PP represents a 13½% aqueous solution of C-12.
QQ represents a 15% aqueous solution of C-12.
RR represents a 15% aqueous solution of equal parts of C-12 and triethanolamine lauryl sulfate.
SS represents a 15% aqueous solution of 3 parts of C-12 to 1 part of triethanolamine lauryl sulfate.
TT represents a 15% aqueous solution of equal parts of C-12 and sodium lauryl sulfate.
UU represents a 15% aqueous solution of 3 parts of C-12 to 1 part of sodium lauryl sulfate.
VV represents a 15% aqueous solution of equal parts of C-12 and ammonium lauryl sulfate.
WW represents a 15% aqueous solution of 3 parts of C-12 to 1 part of ammonium lauryl sulfate.
XX represents a 30% aqueous solution of sodium lauryl sulfate.
YY represents a 30% aqueous solution of ammonium lauryl sulfate.
ZZ represents a 40% solution of triethanolamine lauryl sulfate.

Table

| PRODUCTS | A | B | C | D | E |
|---|---|---|---|---|---|
| Week | | | | | |

Table-continued

| | | | | | | |
|---|---|---|---|---|---|---|
| 1 | <10 | <10 | 0.14* | .006* | .009* | |
| 2 | <10 | <10 | <10 | .002* | <10 | |
| 3 | <10 | <10 | <10 | <10 | <10 | |
| 4 | <10 | <10 | <10 | <10 | <10 | |
| Re-inoculation | | | | | | |
| 5 | <10 | <10 | 1.7* | 1.09* | .009* | |
| 6 | <10 | <10 | 24* | 4.6* | <10 | |
| 7 | <10 | <10 | 57* | 6.9* | <10 | |
| 8 | <10 | <10 | 115* | 8.4* | <10 | |
| PRODUCTS | F | G | H | I | J | |
| Week | | | | | | |
| 1 | <10 | <10 | <10 | <10 | <10 | |
| 2 | <10 | <10 | <10 | <10 | <10 | |
| 3 | <10 | <10 | <10 | <10 | <10 | |
| 4 | <10 | <10 | <10 | <10 | | |
| Re-inoculation | | | | | | |
| 5 | <10 | <10 | <10 | .005* | <10 | |
| 6 | <10 | <10 | <10 | <10 | <10 | |
| 7 | <10 | <10 | <10 | <10 | <10 | |
| 8 | <10 | <10 | <10 | <10 | <10 | |
| PRODUCTS | K | L | M | N | O | |
| Week | | | | | | |
| 1 | <10 | <10 | .08* | <10 | .35* | |
| 2 | <10 | <10 | .02* | <10 | .03* | |
| 3 | <10 | <10 | <10 | <10 | <10 | |
| 4 | <10 | <10 | <10 | <10 | <10 | |
| Re-inoculation | | | | | | |
| 5 | <10 | <10 | .002* | <10 | .07* | |
| 6 | <10 | <10 | 40* | <10 | <10 | |
| 7 | <10 | <10 | <10 | <10 | <10 | |
| 8 | <10 | <10 | <10 | <10 | <10 | |
| PRODUCTS | P | Q | R | S | T | |
| Week | | | | | | |
| 1 | <10 | .01* | <10 | 0.13* | <10 | |
| 2 | <10 | <10 | <10 | 0.009* | <10 | |
| 3 | <10 | <10 | <10 | <10 | <10 | |
| 4 | <10 | <10 | <10 | <10 | <10 | |
| Re-inoculation | | | | | | |
| 5 | <10 | <10 | <10 | .19* | <10 | |
| 6 | <10 | <10 | <10 | .008* | <10 | |
| 7 | <10 | <10 | <10 | <10 | <10 | |
| 8 | <10 | <10 | <10 | <10 | <10 | |
| PRODUCTS | U | V | W | X | Y | Z |
| Week | | | | | | |
| 1 | <10 | <10 | .18* | <10 | .06* | <10 |
| 2 | <10 | <10 | <10 | <10 | .001* | <10 |
| 3 | <10 | <10 | <10 | <10 | <10 | <10 |
| 4 | <10 | <10 | <10 | <10 | <10 | <10 |
| Re-inoculation | | | | | | |
| 5 | <10 | <10 | .007* | <10 | .23* | <10 |
| 6 | <10 | <10 | <10 | <10 | .008* | <10 |
| 7 | <10 | <10 | <10 | <10 | <10 | <10 |
| 8 | <10 | <10 | <10 | <10 | <10 | <10 |
| PRODUCTS | AA | BB | CC | DD | EE | |
| Week | | | | | | |
| 1 | 05* | <10 | <10 | <10 | <10 | |
| 2 | <10 | <10 | <10 | <10 | <10 | |
| 3 | <10 | <10 | <10 | <10 | <10 | |
| 4 | <10 | <10 | <10 | <10 | <10 | |
| Re-inoculation | | | | | | |
| 5 | .03* | <10 | .05* | .002* | <10 | |
| 6 | <10 | <10 | | | <10 | |
| 7 | <10 | <10 | | | <10 | |
| 8 | <10 | <10 | | | <10 | |
| PRODUCTS | FF | GG | HH | II | JJ | |
| Week | | | | | | |
| 1 | <10 | <10 | <10 | <10 | <10 | |
| 2 | <10 | <10 | <10 | <10 | <10 | |
| 3 | <10 | <10 | <10 | <10 | <10 | |
| 4 | <10 | <10 | <10 | <10 | <10 | |

Table-continued

| | | | | | | |
|---|---|---|---|---|---|---|
| Re-inoculation | | | | | | |
| 5 | <10 | <10 | <10 | .003* | <10 | |
| 6 | <10 | <10 | <10 | | <10 | |
| 7 | <10 | <10 | <10 | | <10 | |
| 8 | <10 | <10 | <10 | | <10 | |
| PRODUCTS | KK | LL | MM | NN | OO | |
| Week | | | | | | |
| 1 | <10 | <10 | <10 | <10 | <10 | |
| 2 | <10 | <10 | <10 | <10 | <10 | |
| 3 | <10 | <10 | <10 | <10 | <10 | |
| 4 | <10 | <10 | <10 | <10 | <10 | |
| Re-inoculation | | | | | | |
| 5 | <10 | .04* | <10 | <10 | <10 | |
| 6 | <10 | <10 | <10 | <10 | <10 | |
| 7 | <10 | <10 | <10 | <10 | <10 | |
| 8 | <10 | <10 | <10 | <10 | <10 | |
| PRODUCTS | PP | QQ | RR | SS | TT | |
| Week | | | | | | |
| 1 | <10 | <10 | <10 | <10 | .001* | |
| 2 | <10 | <10 | <10 | <10 | <10 | |
| 3 | <10 | <10 | <10 | <10 | <10 | |
| 4 | <10 | <10 | <10 | <10 | <10 | |
| Re-inoculation | | | | | | |
| 5 | <10 | <10 | <10 | <10 | .003* | |
| 6 | <10 | <10 | <10 | <10 | | |
| 7 | <10 | <10 | <10 | <10 | | |
| 8 | <10 | <10 | <10 | <10 | | |
| PRODUCTS | UU | VV | WW | XX | YY | ZZ |
| Week | | | | | | |
| 1 | <10 | <10 | <10 | 17* | 56* | 29* |
| 2 | <10 | <10 | <10 | 48* | 114* | 86* |
| 3 | <10 | <10 | <10 | 102* | 154* | 118* |
| 4 | <10 | <10 | <10 | 151* | 185* | 250* |
| Re-inoculation | | | | | | |
| 5 | <10 | <10 | <10 | 195* | 252* | 320* |
| 6 | <10 | <10 | <10 | 217* | 480* | 490* |
| 7 | <10 | <10 | <10 | 282* | 670* | |
| 8 | <10 | <10 | <10 | 354* | 940* | |

The invention claimed is:

1. Compound having the structure:

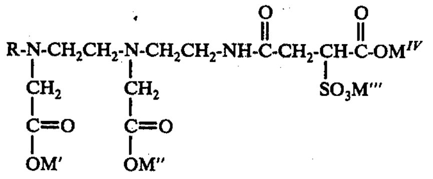

where R is an alkyl group of from 8 to 14 carbon atoms, and where M', M'', M''', and $M^{IV}$ may be the same or different and constitute monovalent moieties selected from the group consisting of hydrogen, alkali metal, ammonium ion, and ammonium ion that is substituted by from 1 to 3 lower alkyl groups, each of from 1 to 3 carbon atoms, and wherein each of said alkyl groups is either unsubstituted or is substituted by one hydroxyl group.

* * * * *